United States Patent
Story et al.

(10) Patent No.: US 9,358,247 B2
(45) Date of Patent: *Jun. 7, 2016

(54) METHODS AND COMPOSITIONS FOR PROMOTING ACTIVITY OF ANTI-CANCER THERAPIES

(71) Applicant: Oncology Research International Limited, Perth (AU)

(72) Inventors: Michael John Story, Carrickalinga (AU); Kenneth Michael Wayte, Ocean Reef (AU)

(73) Assignee: Oncology Research International Limited, Perth (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/476,346

(22) Filed: Sep. 3, 2014

(65) Prior Publication Data

US 2014/0370122 A1    Dec. 18, 2014

Related U.S. Application Data

(63) Continuation of application No. 13/913,220, filed on Jun. 7, 2013, which is a continuation of application No. 12/375,900, filed as application No. PCT/AU2007/001091 on Aug. 3, 2007, now abandoned.

(30) Foreign Application Priority Data

Aug. 3, 2006 (AU) ................. 2006904193

(51) Int. Cl.
| | |
|---|---|
| *A61K 31/58* | (2006.01) |
| *A61K 31/337* | (2006.01) |
| *A61K 31/7048* | (2006.01) |
| *A61K 31/568* | (2006.01) |
| *A61K 31/704* | (2006.01) |
| *A61K 45/06* | (2006.01) |
| *A61K 31/506* | (2006.01) |
| *A61K 31/513* | (2006.01) |
| *A61K 31/475* | (2006.01) |
| *A61K 31/505* | (2006.01) |
| *A61K 33/24* | (2006.01) |
| *A61K 31/437* | (2006.01) |

(52) U.S. Cl.
CPC ........... *A61K 31/7048* (2013.01); *A61K 31/337* (2013.01); *A61K 31/437* (2013.01); *A61K 31/475* (2013.01); *A61K 31/505* (2013.01); *A61K 31/506* (2013.01); *A61K 31/513* (2013.01); *A61K 31/568* (2013.01); *A61K 31/58* (2013.01); *A61K 31/704* (2013.01); *A61K 33/24* (2013.01); *A61K 45/06* (2013.01)

(58) Field of Classification Search
CPC combination set(s) only.
See application file for complete search history.

(56) References Cited

U.S. PATENT DOCUMENTS

| | | | |
|---|---|---|---|
| 6,168,795 B1 | 1/2001 | Djang | |
| 6,444,233 B1 | 9/2002 | Arntzen et al. | |
| 6,759,397 B2 | 7/2004 | Jia | |
| 2002/0045202 A1 | 4/2002 | Korczak et al. | |
| 2003/0087836 A1 | 5/2003 | Huang et al. | |
| 2003/0203856 A1 | 10/2003 | Rosazza et al. | |
| 2004/0185057 A1 | 9/2004 | Kirkby et al. | |
| 2004/0242502 A1 | 12/2004 | Marciani | |
| 2005/0175623 A1* | 8/2005 | Wang | 424/184.1 |
| 2005/0288239 A1 | 12/2005 | Adrian et al. | |
| 2008/0318875 A1 | 12/2008 | Chibber | |

FOREIGN PATENT DOCUMENTS

| | | |
|---|---|---|
| CN | 1237583 | 12/1999 |
| CN | 98114030 | 12/1999 |
| WO | WO 03/055514 | 7/2003 |
| WO | WO 2005/060977 | 7/2005 |
| WO | WO 2006/005581 | 1/2006 |
| WO | WO 2007/003957 | 1/2007 |

OTHER PUBLICATIONS

Pettit et al.; "Antineoplastic Agents. 534. Isolation and Structure of Sansevistatins 1 and 2 from the African Sansevieria ehrenbergii"; J. Nat. Prod.; 2005; 68: 729-733.*
Trump et al.; "Anti-tumor activity of calcitriol: pre-clinical and clinical studies"; 2004; Journal of Steroid Biochemistry & Molecular Biology; 89-90: 519-526.*
Armah et al., "The Membrane-Permeabilizing Effect of Avenacin A-1 Involves the Reorganization of Bilayer Cholesterol," *Biophysical Journal* 76:281-290, Jan. 1999.
Bomford et al., "Adjuvanticity and ISCOM formation by structurally diverse saponins," *Vaccine* 10(9):572-577, 1992.
Broberg et al., "Oligosaccharide sequences of *Quillaja* saponins by electrospray ionization ion trap multiple-stage mass spectrometry," *Journal of Mass Spectrometry* 39:691-701, 2004.
Cai et al., "Apoptosis Induced by Dioscin in Hela Cells," *Biol. Pharm. Bull.*, 25, 193-196, 2002.
Campbell and Peerbaye, "Saponin," $44^{th}$ *Forum in Immunology*, pp. 523-530, 1992.
Cheeke, "Actual and potential applications of *Yucca schidigera* and *Quillaja saponaria* saponins in human and animal nutrition," *Journal of Animal Science* 77:1-10, 2000.
Cheung et al., "Polyphyllin D is a potent apoptosis inducer in drug-resistant HepG2 cells," *Cancer Letters* 217:203-211, 2005.
Francis et al., "The biological action of saponins in animal systems: a review," *British Journal of Nutrition* 88:587-605, 2002.
Gaida et al., "Saponins-Mediated Potentiation of Cisplatin Accumulation and Cytotoxicity in Human Colon Cancer Cells," *Letter . . . Planta Med* 68:70-72, 2002.

(Continued)

Primary Examiner — Timothy Thomas
(74) Attorney, Agent, or Firm — Klarquist Sparkman, LLP

(57) ABSTRACT

The present invention relates to a method of inhibiting growth of a cancerous cell. The method includes the step of exposing the cancerous cell to an anti-cancer therapy and an effective amount of a steroid saponin.

10 Claims, 1 Drawing Sheet

(56) References Cited

OTHER PUBLICATIONS

Gilabert-Oriol et al., "Real-time analysis of membrane permeabilizing effects of oleanane saponins," *Bioorganic & Medicinal Chemistry* 21:2387-2395, 2013.

Hedman, "Intracellular Localization of Fibronectin Using Immunoperoxidase Cytochemistry in Light and Electron Microscopy," *The Journal of Histochemistry and Cytochemistry* 28(11):1233-1241, 1980.

Jalal et al., "Polarized distribution of neutral endopeptidase 21.11 at the cell surface of cultured human intestinal epithelial Caco-2 cells," *Biochem. J.* 288:945-951, 1992.

Jekunen et al., "Modulation of Cisplatin Cytotoxicity by Permeabilization of the Plasma Membrane by Digitonin In Vitro," *Biochemical Pharmacology*, 45(10):2079-2085, 1993.

Kensil et al., "Separation and Characterization of Saponins with Adjuvant Activity from *Quillaja saponaria* Molina Cortex," *The Journal of Immunology* 146(2):431-437, Jan. 15, 1991.

Kim et al., "Hypocholesterolemic Property of *Yucca schidigera* and *Quillaja saponaria* Extracts in Human Body," *Archives of Pharmacal Research* 26(12):1042-1046, 2003.

Lin et al., "New Diosgenin Glycosides from *Costus afer*," *J Nat Prod.*, 60:1165-1169, 1997.

Liu et al., "The Mitotic-Arresting and Apoptosis-Inducing Effects of Diosgenyl Saponins on Human Leukemia Cell Lines," *Biol. Pharm. Bull.*, 27, 1059-1065, 2004.

Mabjeesh et al., "Disruption of Tight Junction Integrity, and Induced Mammary Involution in Lactating Goats by Saponins," *The Open Agriculture Journal* 1:1-4, 2007.

Marciani et al., "Altered immunomodulating and toxicological properties of degraded *Quillaja saponaria* Molina saponins," *International Immunopharmacology* 1:813-818, 2001.

Melzig et al., "Investigations of the mechanism of membrane activity of selected triterpenoid saponins," *Planta Med* 67(1):43-48, 2001.

Mi et al., "Evaluation of the Potential Cancer Chemotherapeutic Efficacy of Natural Product Isolates Employing in Vivo Hollow Fiber Tests," *J. Nat. Prod.*, 65:842-850, 2002.

Nakamura et al., "Cytotoxic Activities of *Solanum* Steroidal Glycosides," *Biol. Pharm. Bull.* 19(4):564-566, 1996.

Nishikawa et al., "Interaction of Digitonin and Its Analogs with Membrane Cholesterol," *J. Biochem.*, 96, 1231-1239, 1984.

Oda et al., "Adjuvant and haemolytic activities of 47 saponins derived from medicinal and food plants," *Biol Chem* 381:67-74, 2000.

Pitha et al., "Digitonin Derivatives of Low Toxicity: Potential Solubilizers for Lipophilic Compounds," *Journal of Pharmaceutical Sciences*, 73, 240-243, Feb. 1984.

Resnik, "Quillaia Extracts," *Chemical and Technical Assessment* 61st JECFA (9 pages), 2004.

"Saponin from Quillaja Bark," http://www.sigmaaldrich.com/etc/medialib/docs/Sigma/Product_Information_Sheet/1/s7900pis.Par.0001.File.tmp/s7900pis.pdf, 2 pages, downloaded prior to Aug. 14, 2012.

Sosman et al., "Molecular Targets in Melanoma from Angiogenesis to Apoptosis," *Clin. Cancer Res.*, 12, 2376s-2383s, Apr. 1, 2006.

Sparg et al., "Biological activities and distribution of plant saponins," *Journal of Ethnopharmacology* 94:219-243, 2004.

Sun et al.,"Advances in saponin-based adjuvants," *Vaccine* 27:1787-1796, 2009.

Wu et al., "Formosanin-C, and Immunomodulator with Antitumor Activity," *Int J. Immunopharmoc.*, 12(7):777-786, 1990.

Supplementary European Search Report for European Application No. EP 07763797.3, dated Mar. 28, 2011 (2 pages).

Aggarwal et al., "Antiangiogenic agents in the management of non-small cell lung cancer," *Cancer Biology & Therapy*, 13:5 247-263, Mar. 2012.

Caglar et al., "A Diverse Stochastic Search Algorithm for Combination Therapeutics," *BioMed Research International*, vol. 2014, 9 pages, Mar. 12, 2014.

Dienstmann et al., "Drug development to overcome resistance to EGFR inhibitors in lung and colorectal cancer," *Molecular Oncology*, vol. 6, 15-26, Dec. 6, 2011.

Johnson, "Targeted Therapies in Combination with Chemotherapy in Non-Small Cell Lung Cancer," *Clin Cancer Res*, vol. 12, 4451-4457, Jul. 15, 2006.

Nartowska et al., "Anti-Angiogenic Activity of Convallamaroside, the Steroidal Saponin Isolated from the Rhizomes and Roots of *Convallaria majalis* L.," *Polish Pharmaceutical Society*, 61:4 (279-282), Nov. 26, 2003.

Nevins, "Pathway-Based Classification of Lung Cancer: a strategy to guide therapeutic selection" *Proc Am Thorac Soc*, vol. 8, 180-182, May 2010.

Scagliotti et al., "Targeting Angiogenesis with Multitargeted Tyrosine Kinase Inhibitors in the Treatment of Non-Small Cell Lung Cancer," *The Oncologist*, vol. 15, 436-446, Apr. 28, 2010.

Shepherd et al., "Lung Cancer in 2013: State of the Art Therapy for Metastatic Disease," *American Society of Clinical Oncology*, 339-346, 2013.

Shishodia et al., "Diosgenin inhibits osteoclastogenesis, invasion, and proliferation through the downregulation of Akt, IκB kinase activation and NF-κB-regulated gene expression," *Oncogene*, vol. 25, 1463-1473, Dec. 5, 2005.

\* cited by examiner

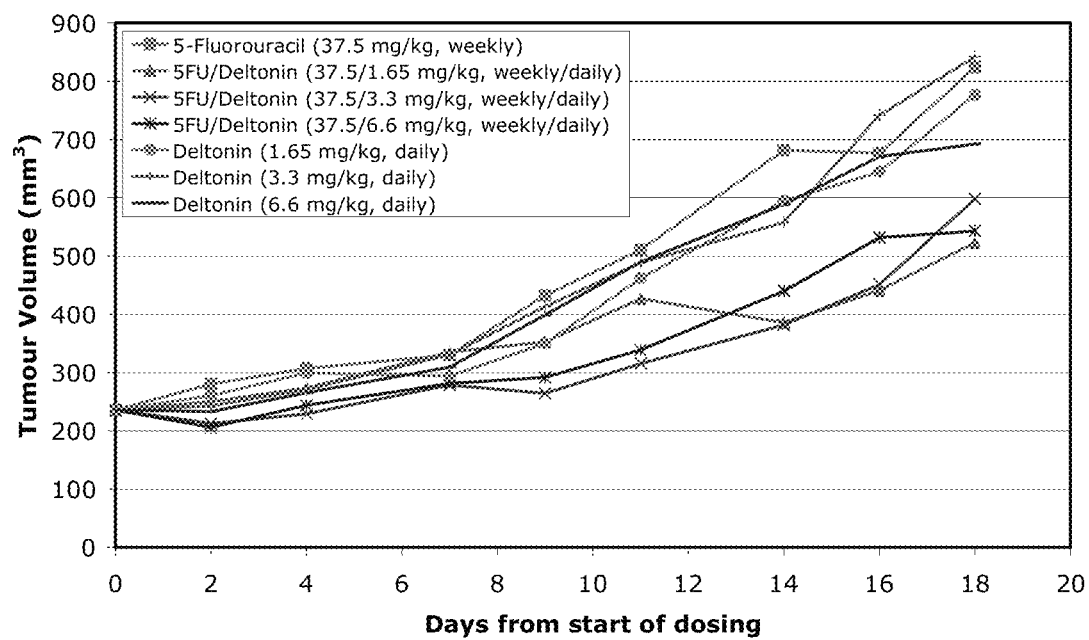

METHODS AND COMPOSITIONS FOR PROMOTING ACTIVITY OF ANTI-CANCER THERAPIES

CROSS REFERENCE TO RELATED APPLICATIONS

This is a continuation of co-pending U.S. patent application Ser. No. 13/913,220, filed Jun. 7, 2013; which is a continuation of U.S. patent application Ser. No. 12/375,900, filed Feb. 21, 2009; which is the U.S. National Stage of International Application No. PCT/AU2007/001091, filed Aug. 3, 2007, which was published in English under PCT Article 21(2); and which in turn claims priority from Australian Provisional Patent Application No. 2006904193 filed on Aug. 3, 2006. Each of these applications is hereby incorporated by reference in its entirety.

FIELD OF THE INVENTION

The present invention relates to methods and compositions for inhibiting the growth of cancerous cells.

BACKGROUND OF THE INVENTION

Chemotherapy and radiation therapy continue to be the main approaches to therapeutic treatment of cancer, with surgery providing the means of physically excising the cancer. More recently, biological agents such as antibodies have been developed as anti-cancer therapies.

The application of many anti-cancer agents and radiation therapy has been based on the premise that the cell death caused by the treatment with these anti-cancer therapies will bring biological processes into play that result in the cancerous cells being ultimately destroyed.

One of these processes is apoptosis. Apoptosis is the complex cellular program of self destruction, triggered by a variety of stimuli that results in self destruction where dying cells shrink, condense and then fragment, releasing small membrane-bound apoptotic bodies that are normally engulfed by other cells such as phagocytes.

Conventional chemotherapeutic agents covalently bond with DNA to form adducts, thereby resulting in DNA damage, and triggering apoptosis. Traditional chemotherapeutic agents suffer from two major disadvantages: (i) they cause severe side effects, because they also affect healthy proliferating cells; and (ii) increased resistance to the agents by the cancerous cells. In this regard, cancer cells have the ability to develop resistance to the chemotherapeutic agents over time, and ultimately may develop multi-drug resistance.

Inhibition of apoptosis in drug resistant tumours not only affects the death-inducing activities of the drug, but also allows for the possibility of cells acquiring additional mutations following DNA damage. In principle, these mutagenised cells can become more malignant and even less sensitive to subsequent therapies, such that treatment of highly resistant tumours containing anti-apoptotic lesions may do more harm than good.

One of the hallmarks of cancer cells is that they evade apoptosis. Disruption of the apoptotic pathway has important effects on the clinical outcome of chemotherapy. In order for chemotherapeutic agents to be effective, cells must be capable of undergoing apoptosis. Apoptosis is therefore a vitally important phenomenon in cancer chemotherapy, because many anti-cancer drugs exert their initial antitumour effect against cancer cells by inducing apoptosis.

However, not only can some chemotherapeutic drugs inhibit apoptosis after a short period of time, but many tumours also have defective apoptotic pathways and as such are inherently more resistant to chemotherapy. Furthermore, although the rate of apoptosis is not necessarily high in tumour tissues, the induction of apoptosis is correlated with tumour response and clinical outcome in cancer patients.

One of the major obstacles to treatment of many types of cancer is the development or presence of resistance to chemotherapeutic agents, such as occurs in non-small cell lung cancer. For example, the development of cisplatin resistance is a major cause of treatment failure. Several mechanisms have been implicated in cisplatin resistance, one of which is altered expression of oncogenes (e.g. Bcl-2) that subsequently suppress apoptotic pathways and may also contribute to development of resistance.

Accordingly there is a need for agents that may be used in conjunction with anti-cancer therapies to enhance their activity against cancerous cells. The present invention relates to the use of steroid saponins to promote the activity of anti-cancer agents and anti-cancer treatments.

A reference herein to a patent document or other matter which is given as prior art is not to be taken as an admission that the document or matter was known or that the information it contains was part of the common general knowledge as at the priority date of any of the claims.

SUMMARY OF THE INVENTION

The present invention arises out of studies into the ability of steroid saponins to inhibit the growth of cancerous cells. In particular, it has been found that steroid saponins enhance the activity of a number of chemotherapeutic and anti-cancer agents to inhibit growth of cancerous cells.

Without being bound by theory, the ability of steroid saponins to enhance the anti-cancer activity of such agents is likely to be due to the ability of the steroid saponin to promote apoptosis in the cancerous cells when used with the anti-cancer therapy. One mechanism for the ability of the steroid saponin to promote apoptosis may be due to the ability of the steroid saponin to target or inhibit molecules that may otherwise suppress apoptosis in cancerous cells.

Thus, the present invention may be used to promote the activity of anti-cancer agents (such as chemotherapeutic agents) and to promote the activity of anti-cancer treatments (such as radiotherapy).

Accordingly, the present invention provides a method of inhibiting growth of a cancerous cell, the method including exposing the cancerous cell to an anti-cancer therapy and an effective amount of a steroid saponin.

The present invention also provides use of a steroid saponin and an anti-cancer agent in the preparation of a medicament for inhibiting growth of a cancerous cell in a subject.

The present invention also provides a method of promoting the activity of an anti-cancer therapy in a subject, the method including exposing the subject to an effective amount of a steroid saponin.

The present invention also provides use of a steroid saponin in the preparation of a medicament for promoting the activity of an anti-cancer therapy in a subject.

The present invention also provides a method of inhibiting formation and/or growth of a tumour in a subject, the method including exposing the subject to an anti-cancer therapy and an effective amount of a steroid saponin.

The present invention also provides use of a steroid saponin and an anti-cancer agent in the preparation of a medicament for inhibiting formation and/or growth of a tumour in a subject.

The present invention also provides a method of preventing and/or treating a cancer in a subject, the method including exposing the subject to an anti-cancer therapy and an effective amount of a steroid saponin.

The present invention also provides use of a steroid saponin and an anti-cancer agent in the preparation of a medicament for preventing and/or treating cancer in a subject.

The present invention also provides a combination product including:
  a steroid saponin; and
  an anti-cancer agent;
the steroid saponin and the anti-cancer agent provided in a form for co-administration to a subject or in a form for separate administration to a subject.

The present invention also provides an anti-cancer composition, the composition including an anti-cancer agent and a steroid saponin.

The present invention also provides a method of reducing the amount of an anti-cancer therapy provided to a subject to prevent and/or treat a cancer in the subject, the method including exposing the subject to an effective amount of a steroid saponin.

The present invention also provides use of a steroid saponin in the preparation of a medicament for reducing the amount of an anti-cancer therapy provided to a subject to prevent and/or treat a cancer.

The present invention also provides a method of preventing and/or treating a cancer in a subject having an increased resistance to an anti-cancer therapy, the method including exposing the subject to an effective amount of a steroid saponin.

The present invention also provides use of a steroid saponin in the preparation of a medicament for preventing and/or treating a cancer in a subject having an increased resistance to an anti-cancer therapy.

The present invention also provides a method of reducing resistance developing in a cancerous cell to an anti-cancer therapy, the method including exposing the cancerous cell to an effective amount of a steroid saponin.

The present invention also provides use of a steroid saponin in the preparation of a medicament for reducing resistance developing in a cancerous cell to an anti-cancer therapy.

The present invention also provides a method of promoting apoptosis of a cancerous cell due to exposure of the cancerous cell to anti-cancer therapy, the method including exposing the cancerous cell to an effective amount of a steroid saponin.

The present invention also provides use of a steroid saponin in the preparation of a medicament for promoting apoptosis of a cancerous cell due to exposure of the cancerous cell to an anti-cancer therapy.

The present invention also provides a pharmaceutical composition including deltonin.

The present invention also provides use of deltonin in the preparation of a medicament.

The present invention also provides a pharmaceutical composition including prosapogenin A.

The present invention also provides use of prosapogenin A in the preparation of a medicament.

The present invention also provides a pharmaceutical composition including asperin.

The present invention also provides use of asperin in the preparation of a medicament.

Various terms that will be used throughout the specification have meanings that will be well understood by a skilled addressee. However, for ease of reference, some of these terms will now be defined.

The term "glycoside" as used throughout the specification is to be understood to mean a compound that contains a saccharide (sugar) moiety (monosaccharide, disaccharide or polysaccharide), linked to a triterpene or steroid or steroid alkaloid aglycone (non-saccharide) component. In most circumstances, the saccharide (sugar) moiety is linked to the C-3 position of the aglycone, although other linkages are contemplated within the scope of the present invention. For example the furostanol glycosides, which contain a saccharide attached to the C-26 position, and spirostanol glycosides are both sub-classes of the steroid saponins.

The term "saponin" as used throughout the specification is to be understood to mean a glycoside including a saccharide (sugar) attached to the aglycone, generally through the C-3 position of the aglycone.

The term "steroid saponin" as used throughout the specification is to be understood to mean a glycoside including one or more saccharide units (including one or more monosaccharide, disaccharide or polysaccharide units) attached to an aglycone which does not contain a nitrogen atom.

In this regard, it will be understood that the term "steroid saponin" includes within its scope any salts or any other derivatives of the compounds that are functionally equivalent in terms of their ability to enhance the activity of an anti-cancer therapy.

A steroid "aglycone" is also called a "genin" or "sapogenin" and the terms may be used interchangeably throughout the specification and all are to be understood to mean the non-saccharide portion of a saponin molecule.

The term "saccharideA-(1→n)-saccharideB" as used throughout the specification is to be understood to mean that saccharideA is linked by its C-1 to the C-n of saccharideB, n being an integer.

For example the polysaccharide with the common name "chacotriose" is α-L-rhamnopyranosyl-(1→2)-[α-L-rhamnopyranosyl-(1→4)]-β-D-glucopyranoside. An abbreviated form of nomencalture in accordance with IUPAC recommendations used herein is Rha 2, [μm 4], Glc.

The term "anti-cancer therapy" as used throughout the specification is to be understood to mean an anti-cancer agent, such as a chemotherapeutic agent (eg cisplatin) or a biological agent (eg an antibody), or an anti-cancer treatment, such as radiotherapy.

The term "subject" as used throughout the specification is to be understood to mean any human or animal subject. In this regard, it will be understood that the present invention includes within its scope veterinary applications. For example, the animal subject may be a mammal, a primate, a livestock animal (eg. a horse, a cow, a sheep, a pig, or a goat), a companion animal (eg. a dog, a cat), a laboratory test animal (eg. a mouse, a rat, a guinea pig, a bird), an animal of veterinary significance, or an animal of economic significance.

The term "treat", and variants thereof as used throughout the specification, is to be understood to mean therapeutic intervention with an effective amount of a steroid saponin. For example, the term includes within its scope therapeutic intervention to have one or more of the following outcomes: (i) inhibit or prevent the growth of a primary tumour in a subject, including reducing the growth of the primary tumour after resection; (ii) inhibit or prevent the growth and formation of one or more secondary tumours in a subject; (iii) improve the life expectancy of the subject as compared to the untreated state; and (iv) improve the quality of life of the subject as compared to the untreated state.

The term "inhibit" as used throughout the specification is to be understood to mean a reduction in the progress of a process, including any one or more of the start, rate, probability, continuation or termination of a process.

The term "cancerous cell" as used throughout the specification in relation to cells is to be understood to mean a cell that is immortalized and whose growth is not contact inhibited by other cells. A cancerous cell may also no longer show a dependence on exogenous growth factors and/or anchorage dependent growth.

The term "biological system" as used throughout the specification is to be understood to mean any multi-cellular system and includes isolated groups of cells to whole organisms. For example, the biological system may be cells in tissue culture, a tissue or organ, or an entire human subject suffering the effects of undesired or uncontrolled growth of cancerous cells.

BRIEF DESCRIPTION OF THE FIGURES

FIG. 1 shows the effect of deltonin on tumour volume in combination with 5-Fluorouracil in HT29 human prostate carcinoma cell subcutaneously introduced into mice.

GENERAL DESCRIPTION OF THE INVENTION

As mentioned above, in one embodiment the present invention provides a method of inhibiting growth of a cancerous cell, the method including exposing the cancerous cell to an anti-cancer therapy and an effective amount of a steroid saponin.

The present invention is based on the finding that steroid saponins have the ability to promote the activity of anti-cancer therapies. Thus a steroid saponin may be used in combination with an anti-cancer therapy to inhibit growth of a cancerous cell.

The cancerous cell in the various embodiments of the present invention may be a human or animal cell.

The cancerous cell may be a cancerous cell present in vivo or in vitro. For example, the cancerous cell may be a cancerous cell present in in vitro cell culture.

In the case of a cell in vitro, the cancerous cell may be a primary cell, such as a cancerous cell isolated or derived from a tumour in a subject. Alternatively, the cancerous cell may be a cell derived from a cancerous cell line. Examples of cancerous cell lines include human melanoma, colon adenocarcinoma (WiDr), mammary carcinoma (MCF7), mouse T-cell lymphoma (WEHI-7), mouse fibrosarcoma (WEHI-164/IC), SKMel28 (melanoma), HT29 (colon), CI80-13S (ovarian), A549 (lung), DU145 (prostate-hormone independent), PC3 (prostate-hormone independent), LNCap (prostate-hormone dependent), K562 (human erythroleukaemia) and MM96L (melanoma).

The cancerous cell in the various forms of the present invention may also be a cell present in a biological system, such as a cancerous cell present in vivo, including a cancerous cell that is associated with a primary tumour and/or one or more secondary tumours in a subject.

In this regard, the term "biological system" is to be understood to mean any multi-cellular system and includes isolated groups of cells to whole organisms. For example, the biological system may be a tissue or organ, or an entire subject, including a subject with cancer.

Accordingly, in another embodiment the present invention provides a method of inhibiting growth of a cancerous cell in a biological system, the method including exposing the cancerous cell to an anti-cancer therapy and an effective amount of a steroid saponin.

In the case of a cancerous cell present in a subject, the cancerous cell may be associated for example with one or more of the following cancers: carcinoma, bladder cancer, bone cancer, brain tumours, breast cancer, cervical cancer, colorectal cancer including cancer of the colon, rectum, anus, and appendix, cancer of the oesophagus, Hodgkin's disease, kidney cancer, cancer of the larynx, leukaemia, liver cancer, lung cancer, lymphoma, melanoma, moles and dysplastic nevi, multiple myeloma, muscular cancer, non-Hodgkin's lymphoma, oral cancer, ovarian cancer, cancer of the pancreas, prostate cancer, sarcoma, skin cancer, stomach cancer, testicular cancer, teratoma, thyroid cancer, and cancer of the uterus.

In one embodiment, the anti-cancer therapy is the exposure of the cancerous cell to an anti-cancer agent, such as a chemotherapeutic agent or a biological agent.

In another embodiment, the anti-cancer therapy is exposure of the cancerous cell to an anti-cancer treatment, such as radiotherapy.

The present invention also provides use of a steroid saponin and anti-cancer agent in the preparation of a medicament for inhibiting growth of a cancerous cell in a subject.

As discussed above, the present invention may used to promote the activity of an anti-cancer therapy in a subject, by exposing the subject to a steroid saponin.

Accordingly, in another embodiment the present invention provides a method of promoting the activity of an anti-cancer therapy in a subject, the method including exposing the subject to an effective amount of a steroid saponin.

A steroid saponin may also be used in the preparation of a medicament for promoting the activity of an anti-cancer agent.

Accordingly, in another embodiment the present invention provides use of a steroid saponin in the preparation of a medicament for promoting the activity of an anti-cancer agent in a subject.

The present invention may also be used to inhibit the formation and/or growth of a tumour in a subject.

Accordingly, in another embodiment the present invention provides a method of inhibiting the formation and/or growth of a tumour in a subject, the method including exposing the subject to an anti-cancer therapy and an effective amount of a steroid saponin.

A steroid saponin and an anti-cancer agent may also be used in the preparation of a medicament for inhibiting the formation and/or growth of a tumour in a subject.

Accordingly, in another embodiment the present invention provides use of a steroid saponin and an anti-cancer agent in the preparation of a medicament for inhibiting growth and/or formation of tumour in a subject.

The tumour in the various embodiment of the present invention may be a primary tumour or a secondary tumour. Thus, the present invention may also be used to inhibit the formation and growth of a primary tumour, and/or be used to inhibit the formation and/or growth of metastases in the subject.

Methods for assessing the formation and/or growth of tumours are known in the art.

The present invention may also be used to prevent and/or treat a cancer in subject.

Accordingly, in another embodiment the present invention provides a method of preventing and/or treating a cancer in a subject, the method including exposing the subject to an anti-cancer therapy and an effective amount of a steroid saponin.

A steroid saponin and an anti-cancer agent may also be used in the preparation of a medicament for preventing and/or treating a cancer in a subject.

Accordingly, in another embodiment the present invention provides use of a steroid saponin and an anti-cancer agent in the preparation of a medicament for preventing and/or treating cancer in a subject.

The subject in the various embodiments of the present invention may be a human or animal subject.

For example, the animal subject may be a mammal, a primate, a livestock animal (eg. a horse, a cow, a sheep, a pig, or a goat), a companion animal (eg. a dog, a cat), a laboratory test animal (eg. a mouse, a rat, a guinea pig, a bird), an animal of veterinary significance, or an animal of economic significance.

In one embodiment, the subject is a human subject.

The inhibition of growth of the cancerous cell in the various embodiments of the present invention is any form of inhibition of proliferation of the cell. For example, the inhibition of proliferation may involve inhibiting the ability of a cell to begin proliferating, continue proliferating; or reducing the probability that a particular cell will begin or continue proliferating.

Inhibition of the growth of a cancerous cell in the various embodiments of the present invention may be assessed by a method known in the art.

For example, for a cancerous cell in vitro, the growth of the cancerous cell may be determined by a suitable proliferation assay, or by a method for assessing the extent of incorporation of tritiated thymidine into cellular DNA over a given period of time.

For a cancerous cell present in vivo, the growth of the cancerous cell may be determined for example by a suitable imaging method known in the art.

As discussed previously herein, the anti-cancer therapy may be exposure to an anti-cancer agent and/or exposure to an anti-cancer treatment.

In one embodiment, the anti-cancer agent is an agent that promotes apoptosis in a cell upon exposure of the agent to the cell. Methods for determining the ability of an agent to promote apoptosis are known in the art.

In one specific embodiment, the anti-cancer agent inhibits the activity of an inhibitor of apoptosis in the cancerous cell, such as one or more of survivin, XIAP, Bcl-2 or Bcl-XL.

In another embodiment, the anti-cancer agent is a chemotherapeutic agent, such as an alkylating agent, including BCNU (carmustine), bisulfan, CCNU (lomustine), chlorambucil, cisplatin, oxiplatin, melphan, mitomycin C, and thiotepa; antimitotic agents including taxol (paclitaxel), docetaxel, vinblastine sulphate, and vincristine sulphate; topoisomerase inhibitors including doxorubicin, daunorubicin, m-AMSA (amsacrine), mitoxantrone, and VP-16 (etoposide); RNA/DNA antimetabolites including 5-fluorouracil and methotrexate; DNA antimetabolites including Ara-C (cytarabine), hydroxyurea (hydroxycarbamide), and thioguanine (tioguanine).

In another embodiment the anti-cancer agent is a cellular process targeting-agent such as imatinib mesylate, trastuzumab, and gefitinib.

Details of administration routes, doses, and treatment regimens of anti-cancer agents are known in the art, for example as described in "Cancer Clinical Pharmacology" (2005) ed. By Jan H. M. Schellens, Howard L. McLeod and David R. Newell, Oxford University Press.

Saponins are conventionally divided into three major classes: (i) triterpene glycosides; (ii) steroidal glycosides; and (iii) steroidal alkaloid glycosides. They all have in common the attachment of one or more sugar units to the aglycone, generally at the C-3 position. Steroid saponins are generally as described in Hostettmann K and Marston A (2005). *Chemistry & pharmacology of natural products: Saponins*. Cambridge University Press.

As discussed previously herein, steroid saponins do not contain a nitrogen atom in the aglycone moiety.

It will be appreciated that the steroid saponin in the various embodiments of the present invention include naturally occurring steroid saponins and non-naturally occurring steroid saponins (ie chemically synthesized steroid saponins) In addition, it will also be appreciated that the steroid saponin in the various embodiments of the present invention also includes pro-drugs of the steroid saponin, derivatives of steroid saponins, including for example, any esters, ketones, carboxylic acids, salts, substituted forms, halogenated forms or other heteroatom containing forms, unsaturated forms, or any other functional derivative.

The saccharide portion of the steroid saponins in the various embodiments of the present invention may include one or more saccharide units, such as a monosaccharide, a disaccharide unit or a polysaccharide unit.

It will also be appreciated that the steroid saponin of the various embodiments of the present invention may also include an aglycone with a saccharide attached at one or more positions of the aglycone moiety.

In one embodiment, the steroid saponin includes a saccharide attached to a single position of the sapogenin component of the steroid saponin.

As discussed above, the saccharide unit may be a monosaccharide, a disaccharide or a polysaccharide. The saccharide may be composed of a suitable monosaccharide, such as D-glucose (Glc), L-rhamnose (Rha), D-galactose (Gal), D-glucuronic acid (GlcA), D-xylose (Xyl), L-arabinose (Ara), D-fucose (Fuc), D-galacturonic acid (GalA). The saccharide unit may also be a substituted sugar, such as an amino sugar, a sulphated sugar, an acylated sugar, a N-acylated sugar, and functional derivatives of any of the aforementioned monosaccharides.

Similarly, a disaccharide may be any combination of two monosaccharides, as described above.

The polysaccharides in the various embodiments of the present invention may be linear or branched, and include any combination of two or more monosaccharide, including the monosaccharide described previously herein.

In one embodiment, the polysaccharide is composed of 1 to 6 monosaccharide units.

In this regard, and as described previously herein, polysaccharides are generally described in the context of the arrangement of the component monosaccharides.

In one embodiment, the saccharide of the steroid saponin is composed of 1 monosaccharide unit. An example of a monosaccharide is glucose with the chemical name β-D-glucopyranoside, which when attached to the aglycone diosgenin via the C-3 position, has the common name of "trillin."

In another embodiment, the saccharide of the steroid saponin is composed of 2 monosaccharide units (ie a disaccharide). An example of a disaccharide is Rha 2, Glc with the chemical name α-L-rhamnopyranosyl(1→2)-β-D-glucopyranoside, which when attached to the aglycone diosgenin via the C-3 position, has the common name of "prosapogenin A."

In another embodiment, the saccharide of the steroid saponin is composed of 3 saccharide units (ie a trisaccharide). Chacotrioside is a common example of a trisaccharide unit, where the glycosyl group of three saccharides comprises two rhamnose units linked to a glucose unit which in turn is linked via a glycosidal linkage to the C-3 position of a sapogenin. Chacotriose is α-L-rhamnopyranosyl-(1→2)-[α-L-rhamnopyranosyl-(1→4)]-β-D-glucopyranoside whereas an abbreviated form of nomencalture in accordance with IUPAC recommendations used herein is Rha 2, [μm 4], Glc.

Similarly solatrioside is a glycosyl group of three saccharides comprising one rhamnose unit and a non-rhamnose saccharide unit, each linked to a third saccharide unit, which is in turn linked via a glycosidal linkage to the C-3 position of a sapogenin.

An example of a tetrasaccharide is [Rha 4, Rha 4], Rha 2, Glc with the chemical name [α-L-rhamnopyranosyl(1→4)-α-L-rhamnopyranosyl(1→4)]-α-L-rhamnopyranosyl(1→2)-β-D-glucopyranoside, which when attached to the aglycone diosgenin via the C-3 position has the common name of "asperin."

Another example of a tetrasaccharide is Glc 4, [Xyl 3], Rha 2, Ara, with the chemical name β-D-glucopyranosyl(14)-[β-D-xylopyranosyl-(1→3)]-α-L-rhamnopyranosyl(1→2)-α-L-arabinoside.

As discussed previously herein, steroid saponins do not contain a nitrogen atom in the aglycone moiety.

Accordingly, it will be appreciated that the steroid saponin in the various embodiments of the present invention will not contain a nitrogen group in the sapogenin moiety, such as not containing a nitrogen in the E and/or F rings of the sapogenin.

In one embodiment, the steroid saponin in the various embodiments of the present is based on a sapogenin with the chemical formula I or II as follows:

Formula I

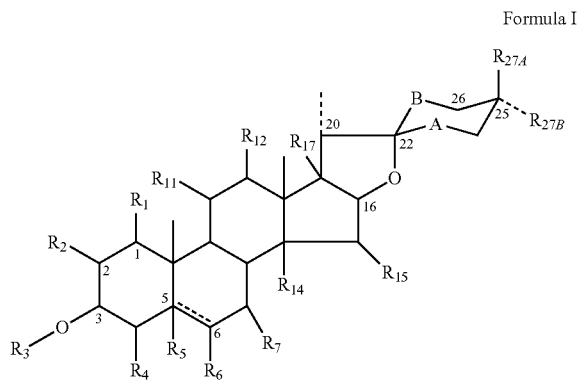

wherein
$R_1$, $R_2$, $R_4$, $R_6$, $R_7$, $R_{11}$, $R_{12}$, $R_{14}$, $R_{15}$ and $R_{17}$ are independently H, OH, =O, pharmacologically acceptable ester groups or pharmacologically acceptable ether groups;
$R_5$ is H when C-5, C-6 is a single bond, and nothing when C-5, C-6 is a double bond;
A is either O concurrently with B being $CH_2$, or B is O concurrently with A being $CH_2$;
$R_{27A}$ is H concurrently with $R_{27B}$ being $CH_3$, or $R_{27A}$ is $CH_3$ concurrently with $R_{27B}$ being H;
$R_3$ comprises a glycosyl group linked through the oxygen atom to the steroidal sapogenin at C-3; or a pharmaceutically acceptable salt, or derivative thereof.

Formula II

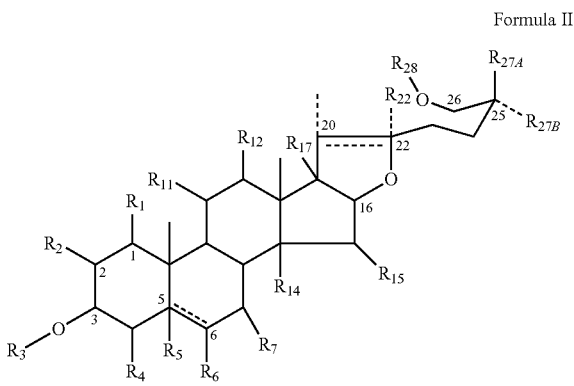

wherein
$R_1$, $R_2$, $R_4$, $R_6$, $R_7$, $R_{11}$, $R_{12}$, $R_{14}$, $R_{15}$ and $R_{17}$ are independently H, OH, =O, pharmacologically acceptable ester groups or pharmacologically acceptable ether groups;
$R_5$ is H when C-5, C-6 is a single bond, and nothing when C-5, C-6 is a double bond;
$R_{22}$ is either a hydroxyl or an alkoxyl group when C-20, C-22 is a single bond, or nothing when C-20, C-22 is a double bond;
$R_{27A}$ is H concurrently with $R_{27B}$ being $CH_3$, or $R_{27A}$ is $CH_3$ concurrently with $R_{27B}$ being H;
$R_{28}$ is H or a saccharide; or a pharmaceutically acceptable salt, or derivative thereof;
$R_3$ comprises a glycosyl group linked through the oxygen atom to the steroidal sapogenin at C-3; or a pharmaceutically acceptable salt, or derivative thereof.

Examples of steroid sapogenins include spirostanol aglycones such as diosgenin, yamogenin (neodiosgenin), yuccagenin, sarsasapogenin, tigogenin, smilagenin, hecogenin, gitogenin, convallamarogenin, neoruscogenin, and solagenin; and furostanol aglycones such as protodiosgenin, pseudoprotodiosgenin, methyl protodiosgenin, protoyamogenin, and methyl protoyamogenin.

In one embodiment, the steroid saponin is a chacotrioside-steroid saponin or a solatrioside-steroid saponin.

Examples of chacotrioside-steroid saponins include "dioscin" which consists of the sapogenin "diosgenin" linked through the C-3 position to chacotriose, diosgenin linked through the C-3 position to another chacotrioside, tigogenin linked through the C-3 position to a chacotrioside, sarsasapogenin linked through the C-3 position to a chacotrioside, smilagenin linked through the C-3 position to a chacotrioside, yuccagenin linked through the C-3 position to a chacotrioside, and yamogenin linked through the C-3 position to a chacotrioside.

Examples of solatrioside steroid saponins include "gracillin", which is diosgenin linked through the C-3 position to the solatrioside (Rha 2, [Glc 3], Glc); "deltonin" (diosgenin linked through the C-3 position to the solatrioside Rha 2, [Glc 4], Glc); diosgenin linked through the C-3 position to solatriose (Rha 2, [Glc 3], Gal) [in this context, diosgenin linked to (Rha 2, [Glc 3], Gal) is termed 'diosgenin solatriose']; diosgenin linked through the C-3 position to another solatrioside; tigogenin linked through the C-3 position to a solatrioside; sarsasapogenin linked through the C-3 position to a solatrioside; smilagenin linked through the C-3 position to a solatrioside; yuccagenin linked through the C-3 position to a solatrioside, and yamogenin linked through the C-3 position to a solatrioside.

Simple monosaccharide steroid saponins are widespread in the plant kingdom. The monosaccharide is generally linked to the aglycone through the C-3 position and examples include "trillin," which is diosgenin linked through the C-3 position to glucose. Other sapogenins linked to glucose through the C-3 position include sarsasapogenin, rhodeasapogenin and yamogenin. Some sapogenins are linked through the C-3 position to another monosaccharide such as arabinose eg, yonogenin and convallagenin or linked through the C-3 position to galactose and so forth.

Examples of disaccharide steroid saponins include sarsasapogenin linked through the C-3 position to for example (Xyl 2, Gal); (Glc 2, Glc); (Glc 3, Glc); smilagenin linked through the C-3 position to (Glc 2, Glc); (Glc 2, Gal); samogenin, tigogenin, gitogenin, alliogenin, ruscogenin, pennogenin, cepagenin and diosgenin linked through the C-3 position to (Rha 2, Glc).

The diosgenin glycosides from Dioscorea species are of great commercial interest as starting materials for steroid hormones. Glycosides of diosgenin and its C-25 isomer yamogenin are among the most frequently documented spirostanol saponins Examples of naturally occurring steroid spirostanol sapogenins with a C-5, C-6 double bond in the B-ring are listed in Table 1:

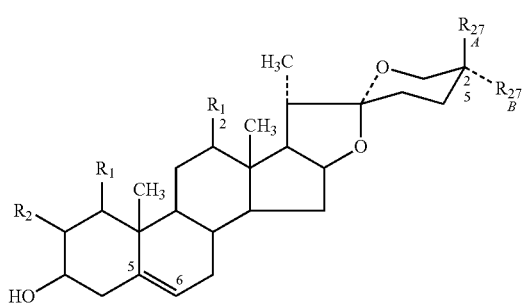

TABLE 1

|  | $R_1$ | $R_2$ | $R_{12}$ | $R_{27A}$ | $R_{27B}$ |
|---|---|---|---|---|---|
| Diosgenin | H | H | H | H | $CH_3$ |
| Yamogenin | H | H | H | $CH_3$ | H |
| Yuccagenin | H | OH | H | H | $CH_3$ |
| Gentrogenin | H | H | =O | H | $CH_3$ |
| Ruscogenin | OH | H | H | H | $CH_3$ |

Examples of naturally occurring steroid spirostanol sapogenins with a C-5, C-6 single bond in the B-ring are listed in Table 2:

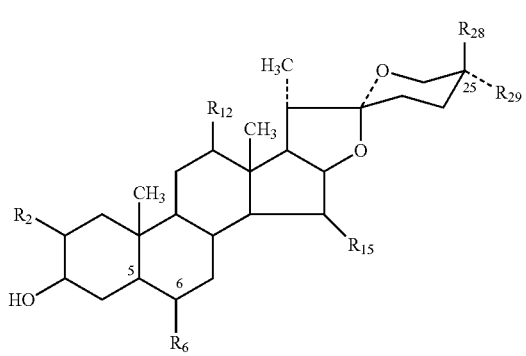

TABLE 2

|  | $R_2$ | $H_5$ | $R_6$ | $R_{12}$ | $R_{15}$ | $R_{28}$ | $R_{29}$ |
|---|---|---|---|---|---|---|---|
| Smilagenin | H | β | H | H | H | H | $CH_3$ |
| Tigogenin | H | α | H | H | H | H | $CH_3$ |
| Sarsasapogenin | H | β | H | H | H | $CH_3$ | H |
| Gitogenin | OH | β | H | H | H | H | $CH_3$ |
| Hecogenin | H | α | H | =O | H | H | $CH_3$ |
| Chlorogenin | H | α | OH(α) | H | H | H | $CH_3$ |
| Digitogenin | OH(α) | α | H | H | OH(β) | H | $CH_3$ |
| Digalogenin | H | α | H | H | OH(β) | H | $CH_3$ |

Examples of naturally occurring steroid furostanol sapogenins of the protospirostane-type with a C-5, C-6 double bond in the B-ring and a C-20, C-22 single bond in the E-ring, are listed in Table 3:

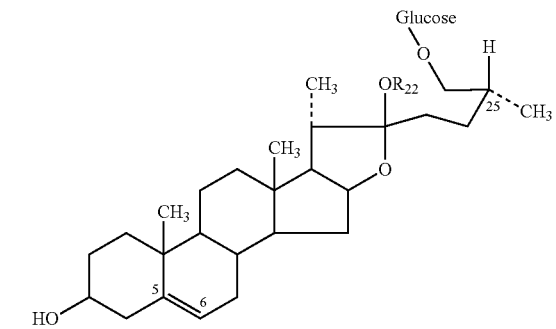

TABLE 3

|  | $R_{22}$ |
|---|---|
| Protodiosgenin | H |
| Methyl protodiosgenin | $CH_3$ |

An example of a naturally occurring steroid furostanol sapogenin of the protospirostane-type with a C-5, C-6 single bond in the B-ring and a C-20, C-22 single bond in the E-ring, is prototigogenin.

An example of a naturally occurring steroid furostanol sapogenin of the pseudospirostane-type with a C-5, C-6 double bond in the B-ring and a C-20, C-22 double bond in the E-ring is pseudodiosgenin.

An example of a naturally occurring steroid furostanol sapogenin of the pseudoprotospirostane-type with a C-5, C-6 double bond in the B-ring and a C-20, C-22 double bond in the E-ring is pseudoprotodiosgenin.

In one embodiment, the steroid saponin is the sapogenin diosgenin linked through the C-3 position to one or more monosaccharide units.

In another embodiment, the steroid saponin is dioscin or gracillin, where dioscin is the sapogenin diosgenin linked through the C-3 position to chacotriose (Rha 2, [μm 4], Glc) and gracillin is diosgenin linked through the C-3 position to the solatrioside (Rha 2, [Glc 3], Glc).

In another embodiment, the steroid saponin is diosgenin linked through the C-3 position to solatriose (Rha 2, [Glc 3], Gal). In this context, diosgenin linked to (Rha 2, [Glc 3], Gal) is termed 'diosgenin solatriose'.

In another embodiment, the steroid saponin is the sapogenin diosgenin linked through the C-3 position to a saccharide.

In another embodiment, the steroid saponin is the sapogenin tigogenin, linked through the C-3 position to a saccharide.

In another embodiment, the steroid saponin is the sapogenin sarsasapogenin, linked through the C-3 position to a saccharide.

In another embodiment, the steroid saponin is the sapogenin smilagenin, linked through the C-3 position to a saccharide.

In another embodiment, the steroid saponin is the sapogenin yuccagenin, linked through the C-3 position to a saccharide.

In another embodiment, the steroid saponin is the sapogenin yamogenin, linked through the C-3 position to a saccharide.

In one specific embodiment, the steroid saponin is selected from the group consisting of deltonin (diosgenin Rha2, [Glc4], Glc), dioscin (diosgenin Rha2, [Rha4], Glc), prosapogenin A (diosgenin Rha2, Glc) and asperin (diosgenin [Rha 4, Rha 4], Rha 2, Glc).

In the case of deltonin, prosapogenin A and asperin, any one of these steroid saponins may be prepared in a pharmaceutical composition.

Accordingly, such steroid saponins may be used in the preparation of a medicament.

Such a medicament may be used for one or more of inhibiting growth of a cancerous cell; inhibiting formation and/or growth of a tumour; preventing and/or treating a cancer, including a cancer having increased resistance to an anti-cancer therapy; promoting the activity of an anti-cancer therapy; reducing the amount of an anti-cancer therapy provided to a subject; promoting apoptosis of a cancerous cell due to exposure of the cell to an anti-cancer therapy; reducing resistance developing in a cancerous cell to an anti-cancer therapy.

As discussed previously herein, the steroid saponin in the various embodiments of the present invention may be obtained from natural sources, manufactured from synthesis processes, or as partial synthesis or modification applied to naturally occurring compounds or intermediates.

The extraction, isolation and identification of steroid saponins in the various embodiments of the present invention may be achieved by methods known in the art.

For example, some steroid saponins may be produced from plant sources. Other sources of steroid saponins may be readily obtained from the literature, for example as described in Hostettmann K and Marston A (2005). *Chemistry & pharmacology of natural products: Saponins*. Cambridge University Press, chapters 1-3 and 6. Common names of steroid saponins have been used in accordance with the above text and the Dictionary of Natural Products, Chapman and Hall, CRC, (2004).

Methods are known in the art for exposing cancerous cells in vitro and in vivo to anti-cancer agents and anti-cancer treatments.

Methods are also known in the art for exposing a steroid saponin to a cancerous cell in vitro and in vivo.

A suitable method for exposing a steroid saponin to the cancerous cell in vitro is by direct exposure of the steroid saponin to the cancerous cell.

In the case of a cancerous cell in a subject, a suitable method of exposing the cancerous cell to the steroid saponin is by administration of the saponin to the subject.

Effective amounts of anti-cancer agents, and effective levels of anti-cancer treatments, are known in the art. Methods for exposing cancerous cells in vitro and in vivo to anti-cancer agents and treatments are known in the art.

The effective amount of the steroid saponin to be exposed to the cancerous cell in the various embodiments of the present invention is not particularly limited. Generally an effective concentration of the steroid saponin will be in the range from $0.1\ \mu M$ to $20\ \mu M$.

In the case of the use of a steroid saponin to enhance the activity of an anti-cancer agent in a subject, the steroid saponin and the anti-cancer agent may be separately administered to the subject in a suitable form, or alternatively, be co-administered to the subject in a suitable form.

For example, the steroid saponin and the anti-cancer agent may be included in a combination product for separate or co-administration to a subject.

Accordingly, in another embodiment the present invention provides a combination product including a steroid saponin and an anti-cancer agent, the steroid saponin and the anti-cancer agent provided in a form for co-administration to a subject or in a form for separate administration to a subject.

The combination product is suitable for, for example, inhibiting the growth of cancerous cells, for inhibiting tumour formation and growth (primary and/or secondary tumours), and for preventing and/or treating a cancer.

The components of the combination product may be packaged separately or together in suitably sterilized containers such as ampoules, bottles, or vials, either in multi-dose or in unit dosage forms. The containers are typically hermetically sealed. Methods are known in the art for the packaging of the components.

As discussed previously herein, co-administration of the steroid saponin and an anti-cancer agent can be sequential or simultaneous and generally means that the agents are present in the subject during a specified time interval. Typically, if a second agent is administered within the half-life of the first agent, the two agents are considered co-administered.

An appropriate dosage regime for the administration of the steroid saponin may be chosen by a person skilled in the art. For example, the administration of the steroid saponin to the subject may be prior to, concurrently with, or after exposure of the subject to the anti-cancer therapy.

In one embodiment, the steroid saponin is administered to a subject concurrently with administration of an anti-cancer agent to a subject, or concurrently with exposure of the subject to an anti-cancer treatment.

In one specific embodiment, the steroid saponin and the anti-cancer agent may be included in a single composition for administration to a subject.

Accordingly, in another embodiment the present invention provides a pharmaceutical composition including a steroid saponin and an anti-cancer agent. In one embodiment, the composition is an anti-cancer composition.

Accordingly, in another embodiment the present invention provides an anti-cancer composition including an anti-cancer agent and a steroid saponin.

The composition may be used, for example, for inhibiting growth of a cancerous cell in vitro or in vivo.

The composition may also be used for inhibiting tumour formation and growth (primary and/or secondary tumours), and for preventing and/or treating a cancer in a subject.

The effective amount of the steroid saponin, and the effective amount of an anti-cancer agent or an anti-cancer treatment, to be administered to the subject is not particularly limited, so long as it is within such an amount and in such a form that generally exhibits a useful or therapeutic effect. The term "therapeutically effective amount" is the quantity which, when administered to a subject in need of treatment, improves the prognosis and/or health state of the subject. The amount to be administered to a subject will depend on the particular characteristics of one or more of the cancerous cell for which growth is to be inhibited, the cancer being treated, the mode of administration, and the characteristics of the subject, such as general health, other diseases, age, sex, genotype, and body weight. A person skilled in the art will be able to determine appropriate dosages depending on these and other factors.

In this regard, details of administration routes, doses, and treatment regimens of anti-cancer agents and radiotherapy treatment are known in the art, for example as described in "Cancer Clinical Pharmacology" (2005) ed. By J. H. M. Schellens, H. L. McLeod and D. R. Newell, Oxford University Press; and "Cancer and its management" (2005). Fifth Edition by R. Souhami and J. Tobias, Blackwell Publishing.

As discussed previously herein, administration and delivery of the compositions according to the present invention may be by, for example, the intravenous, intraperitoneal, subcutaneous, intramuscular, oral, or topical route, or by direct injection into the site of a primary tumour prior to, during or following additional forms of treatment including surgery. The mode and route of administration in most cases will depend on the type of tumour being treated.

The dosage form, frequency and amount of dose will depend on the mode and route of administration. Typically an injectable composition will be administered in an amount of between 5 mg/m$^2$ and 500 mg/m$^2$, generally between 10 mg/m$^2$ and 200 mg/m$^2$. Typically an orally administered composition will be administered in an amount of between 5 mg and 5 g, preferably between 50 mg and 1 g.

For example, effective amounts of the steroid saponin typically range between about 0.1 mg/kg body weight per day and about 1000 mg/kg body weight per day, and in one form between 1 mg/kg body weight per day and 100 mg/kg body weight per day.

As described above, the administration of a composition including a steroid saponin may also include the use of one or more pharmaceutically acceptable additives, including pharmaceutically acceptable salts, amino acids, polypeptides, polymers, solvents, buffers, excipients, preservatives and bulking agents, taking into consideration the particular physical, microbiological and chemical characteristics of the steroid saponins to be administered.

For example, the steroid saponin can be prepared into a variety of pharmaceutical acceptable compositions in the form of, e.g., an aqueous solution, an oily preparation, a fatty emulsion, an emulsion, a lyophilised powder for reconstitution, etc., and can be administered as a sterile and pyrogen free intramuscular or subcutaneous injection or as injection to an organ, or as an embedded preparation or as a transmucosal preparation through nasal cavity, rectum, uterus, vagina, lung, etc. The composition may be administered in the form of oral preparations (for example solid preparations such as tablets, caplets, capsules, granules or powders; liquid preparations such as syrup, emulsions, dispersions or suspensions).

Compositions containing the steroid saponin may also contain one or more pharmaceutically acceptable preservative, buffering agent, diluent, stabiliser, chelating agent, viscosity-enhancing agent, dispersing agent, pH controller, or isotonic agent. These excipients are well known to those skilled in the art.

Examples of suitable preservatives are benzoic acid esters of para-hydroxybenzoic acid, phenols, phenylethyl alcohol or benzyl alcohol. Examples of suitable buffers are sodium phosphate salts, citric acid, tartaric acid and the like. Examples of suitable stabilisers are antioxidants such as alpha-tocopherol acetate, alpha-thioglycerin, sodium metabisulphite, ascorbic acid, acetylcysteine, 8-hydroxyquinoline, and chelating agents such as disodium edetate. Examples of suitable viscosity enhancing agents, suspending, solubilizing or dispersing agents are substituted cellulose ethers, substituted cellulose esters, polyvinyl alcohol, polyvinylpyrrolidone, polyethylene glycols, carbomer, polyoxypropylene glycols, sorbitan monooleate, sorbitan sesquioleate, polyoxyethylene hydrogenated castor oil 60.

Examples of suitable pH controllers include hydrochloric acid, sodium hydroxide, buffers and the like. Examples of suitable isotonic agents are glucose, D-sorbitol or D-mannitol, sodium chloride.

The administration of the steroid saponin in the various embodiments of the present invention may also be in the form of a composition containing a pharmaceutically acceptable carrier, diluent, excipient, suspending agent, lubricating agent, adjuvant, vehicle, delivery system, emulsifier, disintegrant, absorbent, preservative, surfactant, colorant, glidant, anti-adherent, binder, flavorant or sweetener, taking into account the physical, chemical and microbiological properties of the steroid saponin being administered.

For these purposes, the composition may be administered for example orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term parenteral as used herein includes subcutaneous, intravenous, intramuscular, intraperitoneal, intrathecal, intraventricular, intrasternal, and intracranial injection or infusion techniques.

When administered parenterally, the composition will normally be in a unit dosage, sterile, pyrogen free injectable form (solution, suspension or emulsion, which may have been reconstituted prior to use) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable vehicles, dispersing or wetting agents, complexing agents, polymers, solubility aids and suspending agents. The sterile injectable forms may also be sterile injectable solutions or suspensions in non-toxic parenterally acceptable diluents or solvents, for example, as solutions in 1,3-butanediol. Among the pharmaceutically acceptable vehicles and solvents that may be employed are water, ethanol, glycerol, saline, dimethylsulphoxide, N-methylpyrrolidone, dimethylacetamide, Ringer's solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

The carrier may also contain additives, such as substances that enhance solubility, isotonicity, and chemical stability, for example anti-oxidants, buffers and preservatives.

In addition, the composition containing the steroid saponin may be in a form to be reconstituted prior to administration. Examples include lyophilisation, spray drying and the like to produce a suitable solid form for reconstitution with a pharmaceutically acceptable solvent prior to administration.

Compositions may include one or more buffer, bulking agent, isotonic agent and cryoprotectant and lyoprotectant. Examples of excipients include, phosphate salts, citric acid, non-reducing sugars such as sucrose or trehalose, polyhydroxy alcohols, amino acids, methylamines, and lyotropic salts are preferred to the reducing sugars such as maltose or lactose.

When administered orally, the steroid saponin will usually be formulated into unit dosage forms such as tablets, caplets, cachets, powder, granules, beads, chewable lozenges, capsules, liquids, aqueous suspensions or solutions, or similar dosage forms, using conventional equipment and techniques known in the art. Such formulations typically include a solid, semisolid, or liquid carrier. Exemplary carriers include excipients such as lactose, dextrose, sucrose, sorbitol, mannitol, starches, gum acacia, calcium phosphate, mineral oil, cocoa butter, oil of theobroma, alginates, tragacanth, gelatin, syrup, substituted cellulose ethers, polyoxyethylene sorbitan monolaurate, methyl hydroxybenzoate, propyl hydroxybenzoate, talc, magnesium stearate, and the like.

A tablet may be made by compressing or moulding the steroid saponin optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Moulded tablets may be made by moulding in a suitable machine, a mixture of the powdered active ingredient and a suitable carrier moistened with an inert liquid diluent.

The administration of the steroid saponin agent may also utilize controlled release technology.

For topical administration, the composition of the present invention may be in the form of a solution, spray, lotion, cream (for example a non-ionic cream), gel, paste or ointment. Alternatively, the composition may be delivered via a liposome, nanosome, ribosome, or nutri-diffuser vehicle. Topical administration may be used for the treatment of cancers such as melanomas.

It will be appreciated that in the case of the pharmaceutical composition also including an anti-cancer agent, similarly considerations as described above apply to the formulation of the composition.

The present invention may also be used to reduce the amount of an anti-cancer agent or treatment provided to a subject to prevent and/or treat a cancer.

In this regard, the ability of a steroid saponin to increase the level of activity of the anti-cancer therapy can be used to reduce the dose of the anti-cancer therapy exposed to a subject to achieve a desired level of treatment.

Accordingly, in another embodiment the present invention provides a method of reducing the amount of an anti-cancer therapy provided to a subject to prevent and/or treat a cancer in the subject, the method including exposing the subject to an effective amount of a steroid saponin.

The present invention also provides the use of a steroid saponin in the preparation of a medicament for reducing the amount of an anti-cancer therapy provided to a subject to prevent and/or treat a cancer.

Accordingly, in another embodiment the present invention provides use of a steroid saponin in the preparation of a medicament for reducing the amount of an anti-cancer therapy provided to a subject to prevent and/or treat a cancer.

The present invention may also be used to promote apoptosis of a cancerous cell due to exposure of the cell to an anti-cancer agent. For example, the steroid saponin may be used to promote apoptosis of a cell exposed to a chemotherapeutic agent.

Accordingly, in another embodiment the present invention provides a method of promoting apoptosis of a cancerous cell due to exposure of the cancerous cell to an anti-cancer therapy, the method including exposing the cancerous cell to an effective amount of a steroid saponin.

The present invention also provides the use of a steroid saponin in the preparation of a medicament for promoting apoptosis of a cancerous cell due to exposure of the cancerous cell to an anti-cancer therapy.

Accordingly, in another embodiment the present invention provides use of a steroid saponin in the preparation of a medicament for promoting apoptosis of a cancerous cell due to exposure of the cancerous cell to an anti-cancer therapy.

The present invention may also be used to reduce the level of resistance of a cancerous cell to an anti-cancer agent.

For example, exposure of cancerous cells to an anti-cancer agent, such as a chemotherapeutic drug, leads to an increased level of resistance of the cell to the chemotherapeutic drug. Ultimately, this may lead to the cancer developing multi-drug resistance.

Accordingly, in another embodiment the present invention provides a method of reducing resistance developing in a cancerous cell to an anti-cancer therapy, the method including exposing the cancerous cell to an effective amount of a steroid saponin.

The present invention also provides use of the steroid saponin in the preparation of a medicament for reducing resistance developing in a cancerous cell to an anti-cancer therapy.

Accordingly, in another embodiment the present invention also provides use of a steroid saponin in the preparation of a medicament for reducing resistance developing in a cancerous cell to an anti-cancer therapy.

The present invention also provides use of the steroid saponin and the anti-cancer agent in the preparation of a medicament to reduce the level of resistance of a cancerous cell to an apoptotic agent.

Accordingly, in another embodiment the present invention provides use of a steroid saponin in the preparation of a medicament for reducing the level of resistance of a cancerous cell to an anti-cancer agent.

Methods for the preparation of pharmaceutical compositions are known in the art, for example as described in Remington's Pharmaceutical Sciences, 18th ed., 1990, Mack Publishing Co., Easton, Pa.; U.S. Pharmacopeia: National Formulary, 1984, Mack Publishing Company, Easton, Pa.; and M. E. Aulton, Pharmaceutics, The Science of Dosage Form Design, 2nd ed., Churchill Livingstone, Edinburgh, 2002.

Therapeutic delivery of biomolecules is generally as described in Bladon, C. (2002) "Pharmaceutical Chemistry: Therapeutic Aspects of Biomolecules" John Wiley & Sons Ltd.

DESCRIPTION OF SPECIFIC EMBODIMENTS

Reference will now be made to experiments that embody the above general principles of the present invention. However, it is to be understood that the following description is not to limit the generality of the above description.

Example 1

General Reagents and Methods (i) Steroid Saponins and Anti-Cancer Agents

Diosgenin, dioscin: diosgenin Rha2, [Rha4], Glc and deltonin: diosgenin Rha2, [Glc4], Glc were obtained commercially from Ningbo Hanpharm Biotech Co Ltd, and gracillin from ChromaDex, and trillin from Aktin Chemicals.

Prosapogenin A: diosgenin Rha2, Glc was synthesised in accordance with the method described by Li et al *Carbohydr. Res.*, (2001) 331, 1-7. Dioscin and prosapogenin A were also isolated from *Paris polyphylla*.

Steroid saponins were dissolved in dimethylsulphoxide (DMSO) to produce 10 mM or 1 mM stock solutions from which further dilutions were prepared as required for individual experiments.

Cisplatin, docetaxel, paclitaxel, doxorubicin, vincristine and imitanib were obtained from commercial sources and stored either at 4° C. or −20° C. as required. These were: paclitaxel (anzatax injection (Faulding); vincristine sulphate (Sigma); doxorubicin HCl (Sigma); docetaxel (Sigma); cisplatin (Sigma) and imatinib mesylate (Novartis Glivec).

Chemotherapeutic agents were prepared at stock concentrations as required (determined for each assay) in the appropriate diluent: DMSO, sterile water or saline. DMSO solution alone was used as the negative control.

(ii) Cells

Human cancer cell types were: A549 (lung); C180-135 (Ovarian); HT29 (colon); MCF7 (breast); PC3 (prostate); DU145 (prostate, hormone independent); LNCap (hormone dependant); K562 (leukaemia). Mouse cancer cell type was: B16 (melanoma).

Cancer cells were seeded the day before application of drug in triplicate or quadruplicate in 96-well plates, allowed to grow in the presence of drug for 6 days before cell growth relative to untreated control wells was determined with a dye assay.

(iii) Cell Culture

Cells were seeded in triplicate or quadruplicate at 3-4,000 per microtitre well in 90 µl of RPMI culture medium/10% foetal calf serum/penicillin, streptomycin mix, treated with 10 µl of drug (prepared in a dilution plate at 10× concentration required), and allowed to grow until the controls were nearly confluent (6 days).

SRB: Plates were washed with PBS, fixed with methylated spirits, washed with tap water and stained with 50 µL/well of SRB solution (sulforhodamine, 0.4% in 1% acetic acid), followed by washing with tap water and 1% acetic acid, solubilisation in Tris and absorbance read at 564 nm in an ELISA reader.

MTS: 10 µl of MTS solution was added/well of cells, plates allowed to incubate for 1-4 hours at 37° C. until development of a dark brown colour. 10 µl of 10% SDS was then added/well to disperse the cells. Assay plates were then centrifuged at 2000 rpm for 15 minutes and absorbance read at 490 nm in an Elisa reader.

Data was collected using ELISA plate reader software—SOFTmax PRO3.1.2, then imported into EXCEL. The mean and SD of replicates were calculated as a % of control, after subtraction of the blank value (wells with no cells). A graph was plotted of % control vs dose of agent and $IC_{50}$ (half maximal inhibitory concentration) values determined.

Alternatively, cells were seeded into 2 mL wells and following 24 hour growth were treated with steroid saponin at 0.1, 0.5 & 1.0 µM. Cells were harvested after 24, 48 and 72 hour incubation with the drug. At each time point the cells were counted, pelleted by centrifugation (5 minutes, 1500 rpm, RT), resuspended in 1 mL of PBS & vortexed gently. 2 mL of ice cold methanol was added and the cells vortexed. Once cells from all time points were collected, each sample was centrifuged at 12000 rpm for 4-5 minutes, resuspended in 400 µl of PBS and 100 µl of 5× propidium iodide (PI) stain (see below) was added. Samples were vortexed, and filtered through a nylon filter prior to flow cytometry analysis at 488 nm. Relative DNA contents of the cell subpopulations were represented as histograms, with 20,000 cells typically analysed for each sample.

Example 2

Determination of $IC_{50}$ Values for Steroid Saponins and Anti-Cancer Agents

The following cancer cell lines were used:
A549—lung
HT29—colon
MCF7—breast
PC3—prostate (hormone independent)
DU145—prostate (hormone independent)
LNCap—prostate (hormone dependent)
K562—human erythroleukemia The following steroid saponins were assayed for inhibition of cancer cells when used as single agents:
Dioscin: diosgenin Rha2, [Rha4], Glc
Deltonin: diosgenin Rha2, [Glc4], Glc
Prosapogenin A: diosgenin Rha2, Glc The following chemotherapeutic drugs and molecular targeting agents were assayed for inhibition of cancer cells when used as single agents:
Chemotherapeutic agents:
Cisplatin
Docetaxel
Paclitaxel
Doxorubicin
Vincristine
Molecular targeting agent:
Imatinib The steroid saponins and the above-listed anti-cancer agents were dissolved in DMSO and diluted with culture medium into the required solutions for each application. DMSO solution alone was used as the negative control.

Tumour cells were seeded in duplicate in 96-well plates at 2-5,000 per microtitre well containing RPMI culture medium/10% foetal calf serum. The cells were allowed to grow until the controls were nearly confluent after 5-6 days. Plates were then washed with PBS, fixed in ethanol and stained with 50 µL/well of SRB solution (sulforhodamine, 0.4% in 1% acetic acid), followed by washing with 1% acetic acid and solubilisation in Tris. The absorbance was read at 564 nm using an ELISA reader.

The $IC_{50}$, or concentration required to inhibit cell growth by 50%, was determined from the percentage inhibition versus concentration data using the probit calculation methods of Finney (Finney D J (1971). Probit Analysis. $3^{rd}$ Edition. Cambridge University Press).

The following concentrations described in Table 4 were used for the 8 cells of the 12×8 ELISA plates:

TABLE 4

| | Cell concentration (µM) | | | | | | | |
|---|---|---|---|---|---|---|---|---|
| | ELISA Cell | | | | | | | |
| | 1 | 2 | 3 | 4 | 5 | 6 | 7 | 8 |
| Cisplatin | 4 | 2 | 1 | 0.5 | 0.25 | 0.125 | 0.0625 | 0 |
| Docetaxel | 0.006 | 0.003 | 0.0015 | 0.00075 | 0.000375 | 0.000188 | 0.000094 | 0 |
| Paclitaxel | 0.0033 | 0.00167 | 0.00083 | 0.00042 | 0.00021 | 0.000104 | 0.000052 | 0 |

TABLE 4-continued

| | Cell concentration (μM) | | | | | | | |
|---|---|---|---|---|---|---|---|---|
| | ELISA Cell | | | | | | | |
| | 1 | 2 | 3 | 4 | 5 | 6 | 7 | 8 |
| Doxorubicin | 0.2 | 0.1 | 0.05 | 0.025 | 0.0125 | 0.00625 | 0.0031 | 0 |
| Vincristine | 0.02 | 0.01 | 0.005 | 0.0025 | 0.00125 | 0.000625 | 0.00031 | 0 |
| Imatinib | 0.72 | 0.36 | 0.18 | 0.09 | 0.045 | 0.0225 | 0.0112 | 0 |

The following $IC_{50}$ values in Table 5 were estimated from the inhibition data:

TABLE 5

| | $IC_{50}$ (μM) | | | | | | |
|---|---|---|---|---|---|---|---|
| | DU145 | LNCap | MCF7 | HT29 | PC3 | A549 | K562 |
| Cisplatin | 0.54 | 0.70 | 0.65 | 0.93 | 1.4 | 1.2 | 0.82 |
| Docetaxel | 0.00015 | 0.000026 | 0.000039 | 0.00051 | 0.00009 | 0.00027 | 0.00042 |
| Paclitaxel | 0.0027 | 0.0012 | 0.0011 | >0.0033 | 0.0021 | 0.0032 | >0.0033 |
| Doxorubicin | 0.011 | 0.0039 | 0.014 | 0.028 | 0.022 | 0.016 | 0.0085 |
| Vincristine | 0.0029 | 0.00049 | 0.00049 | 0.0024 | 0.0011 | 0.0060 | 0.00021 |
| Imatinib | >0.7 | >0.7 | >0.7 | >0.7 | >0.7 | >0.7 | 0.085 |

Example 3

Determination of $IC_{50}$ Values and Reduction in Dosage of Chemotherapeutic Agent in Mixtures of Steroid Saponins with Cisplatin, Docetaxel, Doxorubicin and Vincristine The cell seeding and ELISA plate methodology of Example 1 were used for determining inhibition of two cancer cell lines. $IC_{50}$ values were determined for the steroid saponins dioscin, deltonin and prosapogenin A, and their mixtures with cisplatin, docetaxel, doxorubicin and vincristine, using LNCap and MCF7 cell lines.

The two-component mixtures were made up by mixing 50% of $IC_{50}$ values for each component where the $IC_{50}$ values of the steroid saponins and chemotherapeutic agents are given in Table 6:

TABLE 6

| | $IC_{50}$ values used in assay (μM) | |
|---|---|---|
| | LNCap | MCF7 |
| Dioscin | 1 | 1 |
| Deltonin | 1 | 1 |
| Prosapogenin A | 2 | 2 |
| Cisplatin | 0.8 | 0.8 |
| Docetaxel | 0.00003 | 0.00003 |

TABLE 6-continued

| | $IC_{50}$ values used in assay (μM) | |
|---|---|---|
| | LNCap | MCF7 |
| Doxorubicin | 0.004 | 0.015 |
| Vincristine | 0.0005 | 0.0005 |

The mixtures were made up as illustrated in Table 7:

TABLE 7

Concentrations used for dioscin and cisplatin in dioscin:cisplatin, 50:50 $IC_{50}$ mixture, against LNCap cell line

| | ELISA Cell | | | | | | | |
|---|---|---|---|---|---|---|---|---|
| | 1 | 2 | 3 | 4 | 5 | 6 | 7 | 8 |
| Multiplying Factor | 8 | 4 | 2 | 1 | 0.5 | 0.25 | 0.125 | 0 |
| Dioscin (μM) | 4 | 2 | 1 | 0.5 | 0.25 | 0.125 | 0.0625 | 0 |
| Cisplatin (μM) | 3.2 | 1.6 | 0.8 | 0.4 | 0.2 | 0.1 | 0.05 | 0 |

Thus, in ELISA cell number 4 (Multiplying Factor=1), the concentration is 50% of each of the individual $IC_{50}$ values: 50% of 1 μM for dioscin and 50% of 0.8 μM for cisplatin.

Table 8 provides a further illustration of setting up ELISA cell concentrations, where in ELISA cell number 4 (Multiplying Factor=1), the concentration is 50% of each of the individual $IC_{50}$ values: 50% of 2 μM for prosapogenin A and 50% of 0.015 μM for doxorubicin against MCF7:

TABLE 8

Concentrations used for dioscin and cisplatin in prosapogenin A:doxorubicin, 50:50 $IC_{50}$ mixture, against MCF7 cell line

| | ELISA Cell | | | | | | | |
|---|---|---|---|---|---|---|---|---|
| | 1 | 2 | 3 | 4 | 5 | 6 | 7 | 8 |
| Multiplying Factor | 8 | 4 | 2 | 1 | 0.5 | 0.25 | 0.125 | 0 |
| Prosapogenin A (μM) | 8 | 4 | 2 | 1 | 0.5 | 0.25 | 0.125 | 0 |
| Doxorubicin (μM) | 0.06 | 0.03 | 0.015 | 0.0075 | 0.00375 | 0.00188 | 0.00094 | 0 |

The inhibitory data from each mixture was used to determine an $IC_{50}$ of $IC_{50}$ value, where the concentrations used were the Multiplying Factor values. In order to determine the actual $IC_{50}$ contribution of each component in the two-component mixture, the $IC_{50}$ of $IC_{50}$ value was multiplied by the $IC_{50}$ of the individual component. This can then be used to determine the reduction in $IC_{50}$ contribution (ie, reduction in dose) of the chemotherapeutic agent due to the presence of the steroid saponin in the mixture. A simpler way of determining the reduction in dose is to use the following simple formula:

$$\text{Reduction in dose (\%)} = \frac{(IC_{50} \text{ of chemotherapeutic agent} - 0.5 \times (IC_{50} \text{ of } IC_{50})) \times 100}{IC_{50} \text{ of chemotherapeutic agent}}$$

The following $IC_{50}$ of $IC_{50}$ values in Table 9 were determined for the steroid saponins of this example:

TABLE 9

|  | LNCap $IC_{50}$ of $IC_{50}$ | MCF7 $IC_{50}$ of $IC_{50}$ |
| --- | --- | --- |
| Dioscin | 0.56 | 1.1 |
| Deltonin | 0.42 | 0.67 |
| Prosapogenin A | 0.89 | 1.1 |

The $IC_{50}$ of $IC_{50}$ values for the chemotherapeutic agents and for their mixtures with the steroid saponins, plus the reduction in dose of each chemotherapeutic agent determined when mixed with the steroid saponins, are given in Table 10:

TABLE 10

| Cisplatin mixtures | | | | |
| --- | --- | --- | --- | --- |
|  | LNCap $IC_{50}$ of $IC_{50}$ | Cisplatin Dose Reduction | MCF7 $IC_{50}$ of $IC_{50}$ | Cisplatin Dose Reduction |
| Cisplatin | 0.37 |  | 0.82 |  |
| Cisplatin + dioscin | 0.54 | 27% | 1.5 | 9% |
| Cisplatin + deltonin | 0.91 | −23% | 1.5 | 9% |
| Cisplatin + prosapogenin A | 1.8 | −143% | 2.2 | −34% |

There was no effective or consistent dose reduction in dosage of cisplatin seen in mixtures of the steroid saponins with cisplatin.

Docetaxel Mixtures

|  | LNCap $IC_{50}$ of $IC_{50}$ | Docetaxel Dose Reduction | MCF7 $IC_{50}$ of $IC_{50}$ | Docetaxel Dose Reduction |
| --- | --- | --- | --- | --- |
| Docetaxel | 3.7 |  | 8 |  |
| Docetaxel + dioscin | 1.3 | 82% | 3.2 | 80% |
| Docetaxel + deltonin | 0.97 | 87% | 1.7 | 89% |
| Docetaxel + prosapogenin A | 2.0 | 73% | 2.0 | 88% |

There was a consistent reduction in dosage of docetaxel seen in mixtures of the steroid saponins with docetaxel.

Doxorubicin Mixtures

|  | LNCap $IC_{50}$ of $IC_{50}$ | Doxorubicin Dose Reduction | MCF7 $IC_{50}$ of $IC_{50}$ | Doxorubicin Dose Reduction |
| --- | --- | --- | --- | --- |
| Doxorubicin | 1.4 |  | 1.6 |  |
| Doxorubicin + dioscin | 0.89 | 68% | 1.3 | 59% |
| Doxorubicin + deltonin | 1.1 | 61% | 2.0 | 38% |
| Doxorubicin + prosapogenin A | 1.7 | 39% | 2.5 | 22% |

There was a reduction in dosage of doxorubicin seen in mixtures of the steroid saponins with doxorubicin, with dioscin and deltonin providing a greater reduction than prosapogenin A.

Vincristine Mixtures

|  | LNCap $IC_{50}$ of $IC_{50}$ | Vincristine Dose Reduction | MCF7 $IC_{50}$ of $IC_{50}$ | Vincristine Dose Reduction |
| --- | --- | --- | --- | --- |
| Vincristine | 0.77 |  | 1.3 |  |
| Vincristine + dioscin | 0.68 | 56% | 1.8 | 31% |
| Vincristine + deltonin | 1.1 | 29% | 1.5 | 42% |
| Vincristine + prosapogenin A | 1.8 | −17% | 2.1 | 19% |

There was a consistent reduction in dosage of doxorubicin seen in mixtures of dioscin and deltonin with vincristine, with prosapogenin A showing effectively zero reduction in vincristine dosage.

Example 4

Determination of $IC_{50}$ Values and Reduction in Dosage of Paclitaxel in Mixtures of Steroid Saponins with Paclitaxel The cell seeding and ELISA plate methodology of Example 2 were used for determining inhibition of two cancer cell lines. $IC_{50}$ values were determined for the steroid saponins dioscin, deltonin and prosapogenin A, and their mixtures with paclitaxel, using A549 and MCF7 cell lines.

The two-component mixtures were made up in the same manner as in Example 3, by mixing 50% of $IC_{50}$ values for each component where the $IC_{50}$ values of the steroid saponins and paclitaxel are given in Table 11:

TABLE 11

| $IC_{50}$ values used in assay (μM) | | |
| --- | --- | --- |
|  | A549 | MCF7 |
| Dioscin | 1 | 1 |
| Deltonin | 1 | 1 |
| Prosapogenin A | 2 | 2 |
| Paclitaxel | 0.003 | 0.001 |

Using the calculation methodology described in Example 3, the following $IC_{50}$ of $IC_{50}$ values in Table 12 were determined for the steroid saponins of this example:

TABLE 12

|  | A549 IC$_{50}$ of IC$_{50}$ | MCF7 IC$_{50}$ of IC$_{50}$ |
|---|---|---|
| Dioscin | 1.9 | 1.9 |
| Deltonin | 0.70 | 1.2 |
| Prosaspogenin A | 0.99 | 1.0 |

The IC$_{50}$ of IC$_{50}$ values for paclitaxel and for its mixtures with the steroid saponins, plus the reduction in dose of paclitaxel determined when mixed with the steroid saponins, are given in Table 13:

TABLE 13

Paclitaxel mixtures

|  | LNCap IC$_{50}$ of IC$_{50}$ | Paclitaxel Dose Reduction | MCF7 IC$_{50}$ of IC$_{50}$ | Paclitaxel Dose Reduction |
|---|---|---|---|---|
| Paclitaxel | 1.7 |  | 1.5 |  |
| Paclitaxel + dioscin | 2.2 | 35% | 1.9 | 37% |
| Paclitaxel + deltonin | 1.0 | 71% | 1.5 | 50% |
| Paclitaxel + prosapogenin A | 2.3 | 32% | 2.3 | 23% |

There was a reduction in dosage of paclitaxel seen in mixtures of the steroid saponins with doxorubicin, with deltonin providing a greater reduction than dioscin and prosapogenin A.

Example 5

Determination of IC$_{50}$ Values and Reduction in Dosage of Chemotherapeutic Agent in Mixtures of Steroid Saponins with Cisplatin, Docetaxel, Doxorubicin and Vincristine The cell seeding and ELISA plate methodology of Example 2 were used for determining inhibition of four cancer cell lines. IC$_{50}$ values were determined for the steroid saponins dioscin, deltonin and prosapogenin A, and their mixtures with cisplatin, docetaxel, doxorubicin and vincristine, using PC3, DU145, A549 and HT29 cell lines.

The two-component mixtures were made up in the same manner as in Example 3, by mixing 50% of IC$_{50}$ values for each component where the IC$_{50}$ values of the steroid saponins and chemotherapeutic agents are given in Table 14:

TABLE 14

IC$_{50}$ values used in assay (μM)

| Dioscin | 1 |
| Deltonin | 1 |
| Prosapogenin A | 2 |
| Cisplatin | 0.8 |
| Docetaxel | 0.0002 |
| Doxorubicin | 0.015 |
| Vincristine | 0.0025 |

Using the calculation methodology described in Example 3, the following IC$_{50}$ of IC$_{50}$ values in Table 15 were determined for the steroid saponins of this example:

TABLE 15

|  | PC3 IC$_{50}$ of IC$_{50}$ | DU145 IC$_{50}$ of IC$_{50}$ | A549 IC$_{50}$ of IC$_{50}$ | HT29 IC$_{50}$ of IC$_{50}$ |
|---|---|---|---|---|
| Dioscin | 2.9 | 1.9 | 2.3 | 2.8 |
| Deltonin | 1.2 | 0.9 | 0.9 | 0.9 |
| Prosapogenin A | 1.5 | 1.5 | 1.5 | 1.5 |

The IC$_{50}$ of IC$_{50}$ values for the chemotherapeutic agents and for their mixtures with the steroid saponins, plus the reduction in dose of each chemotherapeutic agent determined when mixed with the steroid saponins, are given in Tables 16 to 19:

TABLE 16

| Cisplatin mixtures | PC3 IC$_{50}$ of IC$_{50}$ | Cisplatin Dose Reduction | DU145 IC$_{50}$ of IC$_{50}$ | Cisplatin Dose Reduction |
|---|---|---|---|---|
| Cisplatin | 2.7 |  | 1.6 |  |
| Cisplatin + dioscin | 3.5 | 35% | 2.9 | 9% |
| Cisplatin + deltonin | 1.7 | 69% | 1.9 | 41% |
| Cisplatin + prosapogenin A | 2.0 | 63% | 2.1 | 34% |
| Cisplatin mixtures | A549 IC$_{50}$ of IC$_{50}$ | Cisplatin Dose Reduction | HT29 IC$_{50}$ of IC$_{50}$ | Cisplatin Dose Reduction |
| Cisplatin | 1.7 |  | 1.5 |  |
| Cisplatin + dioscin | 3.0 | 12% | 3.0 | 0% |
| Cisplatin + deltonin | 1.7 | 50% | 1.8 | 40% |
| Cisplatin + prosapogenin A | 2.4 | 29% | 2.8 | 7% |

With cisplatin there was a reduction in dosage provided in all cases except for minimal to zero reduction for cisplatin+dioscin with DU145 and with HT29, and minimal reduction for cisplatin+prosapogenin A with HT29.

TABLE 17

| Docetaxel mixtures | PC3 IC$_{50}$ of IC$_{50}$ | Docetaxel Dose Reduction | DU145 IC$_{50}$ of IC$_{50}$ | Docetaxel Dose Reduction |
|---|---|---|---|---|
| Docetaxel | 2.9 |  | 3.1 |  |
| Docetaxel + dioscin | 3.9 | 33% | 3.8 | 39% |
| Docetaxel + deltonin | 2.2 | 62% | 1.9 | 69% |
| Docetaxel + prosapogenin A | 2.6 | 55% | 2.4 | 61% |
| Docetaxel mixtures | A549 IC$_{50}$ of IC$_{50}$ | Docetaxel Dose Reduction | HT29 IC$_{50}$ of IC$_{50}$ | Docetaxel Dose Reduction |
| Docetaxel | 3.9 |  | 3.3 |  |
| Docetaxel + dioscin | 3.8 | 51% | 3.6 | 45% |
| Docetaxel + deltonin | 1.7 | 78% | 1.9 | 71% |
| Docetaxel + prosapogenin A | 3 | 62% | 3 | 55% |

With docetaxel there was a reduction in dosage provided by each of the steroid saponin mixtures with each of the four cell lines as illustrated in Table 17.

TABLE 18

| Doxorubicin mixtures | PC3 IC$_{50}$ of IC$_{50}$ | Doxorubicin Dose Reduction | DU145 IC$_{50}$ of IC$_{50}$ | Doxorubicin Dose Reduction |
|---|---|---|---|---|
| Doxorubicin | 5.5 | | 3.1 | |
| Doxorubicin + dioscin | 5 | 55% | 3.4 | 45% |
| Doxorubicin + deltonin | 2.2 | 80% | 2.3 | 63% |
| Doxorubicin + prosapogenin A | 2.9 | 74% | 2.3 | 63% |

| Doxorubicin mixtures | A549 IC$_{50}$ of IC$_{50}$ | Doxorubicin Dose Reduction | HT29 IC$_{50}$ of IC$_{50}$ | Doxorubicin Dose Reduction |
|---|---|---|---|---|
| Doxorubicin | 3.2 | | 4.7 | |
| Doxorubicin + dioscin | 2.3 | 64% | 3.5 | 63% |
| Doxorubicin + deltonin | 1.8 | 72% | 2.2 | 77% |
| Doxorubicin + prosapogenin A | 2.7 | 58% | 3 | 68% |

With doxorubicin there was a reduction in dosage provided by each of the steroid saponin mixtures with each of the four cell lines as shown in Table 18.

TABLE 19

| Vincristine mixtures | PC3 IC$_{50}$ of IC$_{50}$ | Vincristine Dose Reduction | DU145 IC$_{50}$ of IC$_{50}$ | Vincristine Dose Reduction |
|---|---|---|---|---|
| Vincristine | 3.2 | | 8 | |
| Vincristine + dioscin | 2.3 | 64% | 3.5 | 78% |
| Vincristine + deltonin | 1.3 | 80% | 1.8 | 89% |
| Vincristine + prosapogenin A | 2.7 | 58% | 2.5 | 84% |

| Vincristine mixtures | A549 IC$_{50}$ of IC$_{50}$ | Vincristine Dose Reduction | HT29 IC$_{50}$ of IC$_{50}$ | Vincristine Dose Reduction |
|---|---|---|---|---|
| Vincristine | 8 | | 7.5 | |
| Vincristine + dioscin | 3.1 | 81% | 4.1 | 73% |
| Vincristine + deltonin | 1.7 | 89% | 2.2 | 85% |
| Vincristine + prosapogenin A | 3 | 81% | 3 | 80% |

With vincristine there was a reduction in dosage provided by each of the steroid saponin mixtures with each of the four cell lines as shown in Table 19.

Example 6

Determination of IC$_{50}$ Values and Reduction in Dosage of Imatinib in Mixtures of Steroid Saponins with Imatinib The cell seeding and ELISA plate methodology of Example 2 were used for determining inhibition of the K562 cell line. IC$_{50}$ values were determined for the steroid saponins dioscin, deltonin and prosapogenin A, and their mixtures with imatinib, using the K562 cell line.

The two-component mixtures were made up in the same manner as in Example 3, by mixing 50% of IC$_{50}$ values for each component where the IC$_{50}$ values of the steroid saponins and imatinib are given in Table 20:

TABLE 20

| IC$_{50}$ values used in assay (µM) | |
|---|---|
| Dioscin | 1 |
| Deltonin | 1 |
| Prosapogenin A | 2 |
| Imatinib | 0.09 |

Using the calculation methodology described in Example 3, the following IC$_{50}$ of IC$_{50}$ values were determined for the steroid saponins of this example and shown in Table 21:

TABLE 21

| | K562 IC$_{50}$ of IC$_{50}$ |
|---|---|
| Dioscin | 1.2 |
| Deltonin | 0.69 |
| Prosapogenin A | 1.2 |

The IC$_{50}$ of IC$_{50}$ values for imatinib and for its mixtures with the steroid saponins, plus the reduction in dose of imatinib determined when mixed with the steroid saponins, are given in Table 22:

TABLE 22

| Imatinib mixtures | K562 IC$_{50}$ of IC$_{50}$ | Imatinib Dose Reduction |
|---|---|---|
| Imatinib | 1.6 | |
| Imatinib + dioscin | 1.4 | 56% |
| Imatinib + deltonin | 1.1 | 66% |
| Imatinib + prosapogenin A | 2 | 38% |

With imatinib there was a reduction in dosage provided by each of the steroid saponin mixtures with the K562 cell line.

Example 7

Determination of Degree of In Vivo Enhancement of Anticancer Activity of a Chemotherapeutic Drug when Co-Administered with a Steroid Saponin 5-Fluorouracil (5FU) is the principal chemotherapeutic drug used in treating colon cancer; it is most commonly co-administered with other chemotherapeutic agents. This study compared the co-administration of 5-fluoruracil and deltonin, with administration of mono-administration of both 5-fluorourcil and deltonin.

72 female Balb/c nude female mice were microchipped, weighed and randomised based on body weight into 8 groups with 9 mice per group.

The treatments, which were all formulated in NMP:PEG300:Water (1:9:10, v/v) and administered daily by intravenous injection for 5-fluorouracil and otherwise by intraperitoneal injection, were as given in the following table (NMP=N-methylpyrrolidone):

TABLE 23

| Treatment | Dose | Administration |
|---|---|---|
| 5-Fluoruracil | 37.5 mg/kg | weekly i.p. |
| 5-Fluoruracil + deltonin | 37.5/1.65 mg/kg | weekly i.v./daily i.p. |
| 5-Fluoruracil + deltonin | 37.5/3.3 mg/kg | weekly i.v./daily i.p. |
| 5-Fluoruracil + deltonin | 37.5/6.6 mg/kg | weekly i.v./daily i.p. |

TABLE 23-continued

| Treatment | Dose | Administration |
|---|---|---|
| Deltonin | 1.65 mg/kg | daily i.p. |
| Deltonin | 3.3 mg/kg | daily i.p. |
| Deltonin | 6.6 mg/kg | daily i.p. |

HT29 human prostate carcinoma cells were cultured in RPMI1640 cell culture medium, which was supplemented with 10% FBS and penicillin-streptomycin (50 IU/mL final concentration). The cells were harvested by trypsinisation, washed twice in HBSS and counted. The cells were then resuspended in HBSS and adjusted to a final volume containing $2 \times 10^7$ cells/mL. For inoculation, the needle was introduced through the skin into the subcutaneous space just below the right shoulder, where 100 µL of cells ($2 \times 10^6$) were discharged.

When the tumour volumes had reached an average of greater than 200 mm³, treatment was started (Day 0). Tumour volumes were measured 3-times weekly, and determined according to the formula:

$$V(mm^3) = length \times diameter^2 \times \pi/6$$

Treatment was continued for 17 days. The mean tumour volumes for each dosage regime are given in Table 24 and are presented graphically in FIG. 1:

TABLE 24

| | Days | | | | | | | | |
|---|---|---|---|---|---|---|---|---|---|
| Treatment | 0 | 2 | 4 | 7 | 9 | 11 | 14 | 16 | 18 |
| 5-Fluorouracil (5FU) (37.5 mg/kg) (1 × weekly) | 236 | 280 | 307 | 330 | 432 | 511 | 681 | 676 | 824 |
| 5FU/deltonin (37.5/1.65 mg/kg) (1 × weekly/daily) | 216 | 207 | 249 | 294 | 255 | 339 | 386 | 441 | 523 |
| 5FU/deltonin (37.5/3.3 mg/kg) (1 × weekly/daily) | 235 | 212 | 229 | 278 | 264 | 315 | 381 | 451 | 598 |
| 5FU/deltonin (37.5/6.6 mg/kg) (1 × weekly/daily) | 236 | 206 | 244 | 281 | 292 | 339 | 440 | 532 | 543 |
| Deltonin (1.65 mg/kg) (daily) | 236 | 260 | 299 | 294 | 350 | 462 | 594 | 644 | 776 |
| Deltonin (3.3 mg/kg) (daily) | 236 | 242 | 271 | 331 | 413 | 489 | 558 | 742 | 842 |
| Deltonin (6.6 mg/kg) (daily) | 235 | 233 | 265 | 310 | 399 | 490 | 588 | 671 | 692 |

The tumour volumes with the combined treatments of deltonin with 5-fluorouracil are less than the tumour volumes of any of the mono-treatments, that is, 5-fluorouracil alone, or any of the 3 deltonin treatments alone.

Finally, it will be appreciated that various modifications and variations of the methods and compositions of the invention described herein will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are apparent to those skilled in the art are intended to be within the scope of the present invention.

We claim:

1. A method of inhibiting growth of a cancerous cell, the method including exposing the cancerous cell to docetaxel and a therapeutically effective amount of prosapogenin A, wherein the cancerous cell is a prostate cancer cell, a breast cancer cell, a colon cell, or a lung cancer cell.

2. The method of claim 1, wherein exposing the cancerous cell to the therapeutically effective amount of prosapogenin A reduces an amount of the docetaxel effective for treatment by 55% to 88% as compared to an amount of the docetaxel that would be used without the therapeutically effective amount of prosapogenin A.

3. The method of claim 1, wherein the method is used to inhibit formation and/or growth of a prostate, breast, colon, or lung tumor in a subject.

4. The method of claim 1, wherein the method is used to treat a prostate, breast, colon, or lung cancer in a subject.

5. A method of reducing a therapeutic amount of docetaxel for treating a cancer in a subject, comprising exposing the subject to a therapeutic amount of prosapogenin A, wherein the prosapogenin A reduces the amount of docetaxel to which the subject is exposed.

6. The method of claim 5, wherein the therapeutic amount of docetaxel is reduced by 55% to 88% as compared to a therapeutic amount of docetaxel that would be used without the therapeutically effective amount of pro sapogenin A.

7. The method of claim 1, wherein the cancerous cell is a lung cancer cell.

8. The method of claim 1, wherein the cancerous cell is a prostate cancer cell.

9. The method of claim 1, wherein the cancerous cell is a breast cancer cell.

10. The method of claim 1, wherein the cancerous cell is a colon cancer cell.

* * * * *